United States Patent
Wen

(10) Patent No.: US 7,293,988 B2
(45) Date of Patent: Nov. 13, 2007

(54) ACCURATELY PREDICTING AND PREVENTING INTERFERENCE BETWEEN TOOTH MODELS

(75) Inventor: Huafeng Wen, Redwood City, CA (US)

(73) Assignee: Align Technology, Inc., Santa Clara, CA (US)

( * ) Notice: Subject to any disclaimer, the term of this patent is extended or adjusted under 35 U.S.C. 154(b) by 439 days.

(21) Appl. No.: 11/013,155

(22) Filed: Dec. 14, 2004

(65) Prior Publication Data

US 2006/0127856 A1 Jun. 15, 2006

(51) Int. Cl.
*A61C 3/00* (2006.01)
*A61C 5/00* (2006.01)
(52) U.S. Cl. ......................................... 433/24; 433/215
(58) Field of Classification Search .................... 433/24
See application file for complete search history.

(56) References Cited

U.S. PATENT DOCUMENTS

2004/0214128 A1* 10/2004 Sachdeva et al. ............. 433/24
2005/0177266 A1* 8/2005 Kopelman et al. .......... 700/117

* cited by examiner

*Primary Examiner*—Cris Rodriguez
*Assistant Examiner*—Candice C Stokes
(74) *Attorney, Agent, or Firm*—Paul, Hastings, Janofsky & Walker LLP

(57) ABSTRACT

Systems and methods for preventing interference between two physical tooth models in a physical dental arch model includes digitally representing the surfaces of each of the two physical tooth models by a mesh of points in three dimensions, interpolating the meshes of points to produce interpolated surfaces to represent the boundaries of the two physical tooth models, wherein the interpolated surfaces representing the boundaries of the two physical tooth models intersect at least at one point to form an overlapping portion. The method also includes specifying a straight line running through the overlapping portion and intersecting the two interpolated surfaces representing the boundaries of the two physical tooth models and calculating the length of the straight line in the overlapping portion to quantify the interference between the two physical tooth models.

20 Claims, 26 Drawing Sheets

ACCURATELY PREDICTING AND PREVENTING INTERFERENCE BETWEEN TOOTH MODELS

CROSS-REFERENCES TO RELATED INVENTIONS

The present invention is also related to commonly assigned U.S. Patent Application, titled "A base for physical dental arch model" by Huafeng Wen, filed November 2004, commonly assigned U.S. Patent Application, titled "Accurately producing a base for physical dental arch model" by Huafeng Wen, filed November 2004, commonly assigned U.S. Patent Application, titled "Fabricating a base compatible with physical dental tooth models" by Huafeng Wen, filed November 2004, commonly assigned U.S. Patent Application, titled "Producing non-interfering tooth models on a base" by Huafeng Wen, filed November 2004, commonly assigned U.S. Patent Application, titled "System and methods for casting physical tooth model" by Huafeng Wen, filed November 2004, commonly assigned U.S. Patent Application, titled "Producing a base for accurately receiving dental tooth models" by Huafeng Wen, and filed November 2004, commonly assigned U.S. Patent Application, titled "Producing accurate base for dental arch model" by Huafeng Wen, filed November 2004.

The present invention is also related to U.S. Patent Application, titled "Method and apparatus for manufacturing and constructing a physical dental arch model" by Huafeng Wen, Nov. 1, 2004, U.S. Patent Application, titled "Method and apparatus for manufacturing and constructing a dental aligner" by Huafeng Wen, Nov. 1, 2004, U.S. Patent Application, titled "Producing an adjustable physical dental arch model" by Huafeng Wen, Nov. 1, 2004, and U.S. Patent Application, titled "Producing a base for physical dental arch model" by Huafeng Wen, Nov. 1, 2004. The disclosure of these related applications are incorporated herein by reference.

TECHNICAL FIELD

This application generally relates to the field of dental care, and more particularly to a system and a method for manufacturing and constructing physical tooth models.

BACKGROUND

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is impossible for a human being to accurately develop a visual three-dimensional image of an orthodontic structure due to the limitations of human sight and the physical structure of a human mouth. In addition, it is humanly impossible to accurately estimate three-dimensional wire bends (with an accuracy within a few degrees) and to manually apply such bends to a wire. Further, it is humanly impossible to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontic is very much an art, relying on the expert opinions and judgments of the orthodontist. In an effort to shift the practice of orthodontic from an art to a science, many innovations have been developed. For example, U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Kuroda et al. (1996) Am. J. Orthodontics 110:365-369 describes a method for laser scanning a plaster dental cast to produce a digital image of the cast. See also U.S. Pat. No. 5,605,459. U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the arch is described in U.S. Pat. Nos. 5,342,202 and 5,340,309.

Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

The key to efficiency in treatment and maximum quality in results is a realistic simulation of the treatment process. Today's orthodontists have the possibility of taking plaster models of the upper and lower arch, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per arch that covers all brackets and relevant portions of every tooth. Using such a transfer tray guarantees a very quick and yet precise bonding using indirect bonding.

U.S. Pat. No. 5,431,562 to Andreiko et al. describes a computerized, appliance-driven approach to orthodontics. In this method, first certain shape information of teeth is acquired. A uniplanar target arcform is calculated from the shape information. The shape of customized bracket slots, the bracket base, and the shape of the orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, Align Technologies began offering transparent, removable aligning devices as a new treatment modality in orthodontics. In this system, an impression model of the dentition of the patient is obtained by the orthodontist and shipped to a remote appliance manufacturing center, where it is scanned with a CT scanner. A computer model of the dentition in a target situation is generated at the appliance manufacturing center and made available for viewing to the orthodontist over the Internet. The orthodontist indicates changes they wish to make to individual tooth positions. Later, another virtual model is provided over the Internet and the orthodontist reviews the revised model, and indicates any further changes. After several such iterations, the target situation is agreed upon. A series of removable aligning devices or shells are manufactured and delivered to the orthodontist. The shells, in theory, will move the patient's teeth to the desired or target position.

U.S. Pat. No. 6,699,037 Align Technologies describes an improved methods and systems for repositioning teeth from an initial tooth arrangement to a final tooth arrangement. Repositioning is accomplished with a system comprising a series of appliances configured to receive the teeth in a cavity and incrementally reposition individual teeth in a series of at least three successive steps, usually including at least four successive steps, often including at least ten steps, sometimes including at least twenty-five steps, and occasionally including forty or more steps. Most often, the methods and systems will reposition teeth in from ten to twenty-five successive steps, although complex cases involving many of the patient's teeth may take forty or more steps. The successive use of a number of such appliances permits each appliance to be configured to move individual teeth in small increments, typically less than 2 mm, preferably less than 1 mm, and more preferably less than 0.5 mm. These limits refer to the maximum linear translation of any point on a tooth as a result of using a single appliance. The movements provided by successive appliances, of course, will usually not be the same for any particular tooth. Thus, one point on a tooth may be moved by a particular distance as a result of the use of one appliance and thereafter moved by a different distance and/or in a different direction by a later appliance.

The individual appliances will preferably include a polymeric shell having the teeth-receiving cavity formed therein, typically by molding as described below. Each individual appliance will be configured so that its tooth-receiving cavity has a geometry corresponding to an intermediate or end tooth arrangement intended for that appliance. That is, when an appliance is first worn by the patient, certain of the teeth will be misaligned relative to an undeformed geometry of the appliance cavity. The appliance, however, is sufficiently resilient to accommodate or conform to the misaligned teeth, and will apply sufficient resilient force against such misaligned teeth in order to reposition the teeth to the intermediate or end arrangement desired for that treatment step.

The fabrication of aligners by Align Technologies utilizes stereo lithography process as disclosed in U.S. Pat. Nos. 6,471,511 and 6,682,346. Several drawbacks exist however with the stereo lithography process. The materials used by stereo lithography process may be toxic and harmful to human health. Stereo lithography process builds the aligner mold layer by layer causing the resulting aligners to have a stairmaster like spacing between the layers and such spacing has a tendency house germs and bacteria while it is worn by a patient. Furthermore, stereo lithography process used by Align Technology also requires a different aligner mold at each stage of the treatment, which produces waste and is environmental unfriendly.

The practice of orthodontics and other dental treatments including preparation of a denture can benefit from a physical dental arch model that is representative of the dentition and the alveolar ridge of a patient to be orthodontically treated. The physical dental arch model, also referred as a physical dental arch model, is often prepared based on an impression model. The physical dental arch model is generally prepared by cutting and arranging individual teeth on the alveolar ridge of the impression model. With this physical dental arch model so prepared, not only is a final goal for the dental treatment made clear, but also the occlusal condition between the maxillary and the mandibular dentitions can be ascertained specifically.

Also, the patient when the physical dental arch model is presented can visually ascertain the possible final result of orthodontic treatment he or she will receive and, therefore, the physical dental arch model is a convenient tool in terms of psychological aspects of the patient.

Making a model for a whole or a large portion of an arch is much more difficult than making one tooth abutment for implant purposes. Single teeth do not have the kind of concavities and complexities as in the inter-proximal areas of teeth in an arch. Some prior art making the physical dental arch model is carried out manually, involving not only a substantial amount of labor required, but also a substantial amount of time. It is also extremely difficult to machine an accurate arch model because of the various complex shapes and the complex features such as inter-proximal areas, wedges between teeth, etc. in an arch. There is therefore a long felt need for a practical, effective and efficient method to produce a physical dental arch model.

SUMMARY OF THE INVENTION

The present invention has been devised to provide a practical, effective and efficient methods and apparatus to manufacture and construct the physical dental arch model.

In one aspect, the present invention relates to a method for preventing interference between two physical tooth models in a physical dental arch model, comprising:

digitally representing the surfaces of each of the two physical tooth models by a mesh of points in three dimensions;

interpolating the meshes of points to produce interpolated surfaces to represent the boundaries of the two physical tooth models, wherein the interpolated surfaces representing the boundaries of the two physical tooth models intersect at least at one point to form an overlapping portion;

specifying a straight line running through the overlapping portion and intersecting the two interpolated surfaces representing the boundaries of the two physical tooth models; and calculating the length of the straight line in the overlapping portion to quantify the interference between the two physical tooth models.

In another aspect, the present invention relates to a method for preventing interference between two physical tooth models in a physical dental arch model, comprising:

digitally representing the surfaces of each of the two physical tooth models by a mesh of points in three dimensions;

interpolating the meshes of points to produce interpolated surfaces to represent the boundaries of the two physical tooth models, wherein the interpolated surfaces representing the two physical tooth models intersect at least at one point to form an overlapping portion;

developing aligned coordinate systems or a common coordinate system for the two interpolated surfaces representing the two physical tooth models;

specifying a straight line running through the overlapping portion and intersecting the two interpolated surfaces representing the boundaries of the two physical tooth models; and calculating the length of the straight line in the overlapping portion to quantify the interference between the two physical tooth models.

In yet another aspect, the present invention relates to a method for preventing interference between two physical tooth models in a physical dental arch model, comprising:

digitally representing the surfaces of each of the two physical tooth models by a mesh of points in three dimensions;

interpolating the meshes of points to produce interpolated surfaces to represent the boundaries of the two physical tooth models, wherein the interpolated surfaces representing the boundaries of two physical tooth models intersect at least at one point to form an overlapping portion;

specifying three orthogonally oriented straight lines each running through the overlapping portion and intersecting the two interpolated surfaces representing the boundaries of the two physical tooth models;

calculating the lengths of three orthogonally oriented straight lines in the overlapping portion;

defining three vectors along the three orthogonally oriented straight lines, each of the vectors having a magnitude of the inverse of the corresponding length of the overlapping portion;

calculating a vector sum of the three vectors to determine the direction and the distance required for the interpolated surfaces representing the boundaries of the two physical tooth models to move apart to avoid interference between the two physical tooth models; and moving apart the interpolated surfaces representing the boundaries of the two physical tooth models in accordance to the vector sum to avoid interference between the two physical tooth models.

Embodiments may include one or more of the following advantages. An advantage of the present invention is that adjacent physical tooth models in a physical dental arch model can be simulated. The interference between the two physical models can be predicted before they are assembled to form a physical arch model. The positions and the orientations of the tooth models can be adjusted to prevent the interference. As a result, the precision and effectiveness of the orthodontic treatments are improved.

Another advantage of the present invention is that the physical tooth models can be used to form different tooth arch models having different teeth configurations. The pin configurations can be modified without changing the tooth models themselves to be modified to prevent interference between adjacent tooth models at different steps of an orthodontic treatment. Moreover, the tooth models can be reused as tooth positions are changed during a treatment process. Much of the cost of making multiple tooth arch models in orthodontic treatment are therefore eliminated. The tooth models can have pins that assist their assembling with a base.

Another advantage of the present invention is that the same base can support different tooth arch models having different teeth configurations. The base can include more than one sets of receiving features that can receive tooth models at different positions. The reusable base further reduces cost in the dental treatment of teeth alignment. Furthermore, the receiving features can be modified to receive tooth models having different pin configurations to avoid interference between the adjacent tooth models in a tooth arch model.

The physical tooth models include features to allow them to be attached, plugged or locked to a base. The physical tooth models can be pre-fabricated having standard registration and attaching features for assembling. The physical tooth models can be automatically assembled onto a base by a robotic arm under computer control.

The physical dental arch model obtained by the disclosed system and methods can be used for various dental applications such as dental crown, dental bridge, aligner fabrication, biometrics, and teeth whitening. The arch model can be assembled from segmented manufacturable components that can be individually manufactured by automated, precise numerical manufacturing techniques.

The physical tooth models in the physical dental arch model can be easily separated, repaired or replaced, and reassembled after the assembly without the replacement of the whole arch model. The manufacturable components can be attached to a base. The assembled physical dental arch model specifically corresponds to the patient's arch. There is no need for complex and costly mechanisms such as micro-actuators for adjusting multiple degrees of freedom for each tooth model. The described methods and system is simple to make and easy to use.

The details of one or more embodiments are set forth in the accompanying drawing and in the description below. Other features, objects, and advantages of the invention will become apparent from the description and drawings, and from the claims.

BRIEF DESCRIPTION OF THE DRAWINGS

The accompanying drawing, which are incorporated in and form a part of this specification, illustrate embodiments of the invention and, together with the description, serve to explain the principles of the invention:

FIG. 13(*b*) is a perspective bottom view of two tooth models having pin configurations of FIG. 12.

DESCRIPTION OF INVENTION

Figure 1:
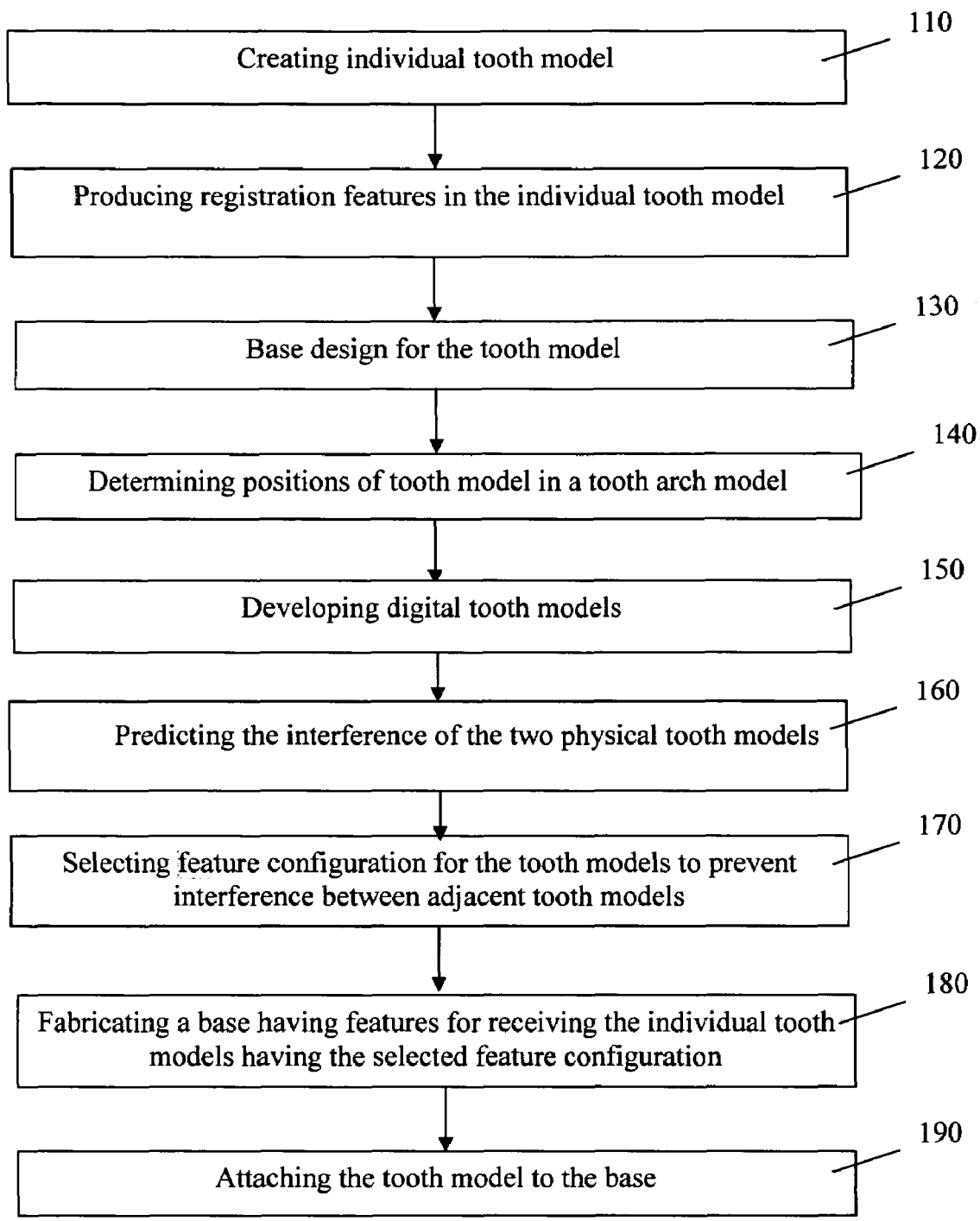
FIG. 1 is a flow chart for producing a physical dental arch model in accordance with the present invention.

Major operations in producing a physical dental arch model are illustrated in FIG. 1. The process generally includes the following steps. First individual tooth model is created in step 110. An individual tooth model is a physical model that can be part of a physical tooth arch model, which can be used in various dental applications. Registration features are next added to the individual tooth model to allow them to be attached to each other or a base in step 120. A base is designed for receiving the tooth model in step 130. The tooth model positions in a tooth arch model are next determined in step 140. The digital tooth models are developed in step 150. The interference between the physical tooth models is predicted in step 160. In step 170, the pin configurations affixed to the tooth models are selected to prevent interference between adjacent tooth models when they are mounted on the base. A base is fabricated in step 180. The base includes features for receiving the individual tooth model having the selected pin configurations. The tooth models are finally attached to the base at the predetermined positions using the pre-designed features in step 190.

Details of process in FIG. 1 are now described. Individual tooth model can be obtained in step 110 in a number of different methods. The tooth model can be created by casting. A negative impression is first made from a patient's arch using for example PVS. A positive of the patient's arch is next made by pouring a casting material into the negative impression. After the material is dried, the mould is then taken out with the help of the impression knife. A positive of the arch is thus obtained.

In an alternative approach, the negative impression of the patient's arch is placed in a specially designed container. A casting material is then poured into the container over the impression to create a model. A lid is subsequently placed over the container. The container is opened and the mould can be removed after the specified time.

Examples of casting materials include auto polymerizing acrylic resin, thermoplastic resin, light-polymerized acrylic resins, polymerizing silicone, polyether, plaster, epoxies, or a mixture of materials. The casting material is selected based on the uses of the cast. The material should be easy for cutting to obtain individual tooth model. Additionally, the material needs to be strong enough for the tooth model to take the pressure in pressure form for producing a dental aligner. Details of making a dental aligner are disclosed in commonly assigned and above referenced U.S. Patent Application titled "Method and apparatus for manufacturing and constructing a dental aligner" by Huafeng Wen, filed Nov. 2, 2004, the content of which is incorporated herein by reference.

Features that can allow tooth models to be attached to a base (step 120) can be added to the casting material in the casting process. Registration points or pins can be added to each tooth before the casting material is dried. Optionally, universal joints can be inserted at the top of the casting chamber using specially designed lids, which would hang the universal joints directly into the casting area for each tooth.

Still in step 110, individual tooth models are next cut from the arch positive. One requirement for cutting is to obtain individual teeth in such a manner that they can be joined again to form a tooth arch. The separation of individual teeth from the mould can be achieved using a number of different cutting methods including laser cutting and mechanical sawing.

Separating the positive mould of the arch into tooth models may result in the loss of the relative 3D coordinates of the individual tooth models in an arch. Several methods are provided in step 120 for finding relative position of the tooth models. In one embodiment, unique registration features are added to each pair of tooth models before the positive arch mould is separated. The separated tooth models can be assembled to form a physical dental arch model by matching tooth models having the same unique registration marks.

The positive arch mould can also be digitized by a three-dimensional scanning using a technique such as laser scanning, optical scanning, destructive scanning, CT scanning and Sound Wave Scanning. A digital dental arch model is therefore obtained. The digital dental arch model is subsequently smoothened and segmented. Each segment can be physically fabricated by CNC based manufacturing to obtain individual tooth models. The digital dental arch model tracks and stores the positions of the individual tooth models. Unique registration marks can be added to the digital tooth models that can be made into a physical feature in CNC base manufacturing.

Examples of CNC based manufacturing include CNC based milling, Stereolithography, Laminated Object Manufacturing, Selective Laser Sintering, Fused Deposition Modeling, Solid Ground Curing, 3D ink jet printing. Details of fabricating tooth models are disclosed in commonly assigned and above referenced U.S. Patent Application titled "Method and apparatus for manufacturing and constructing a physical dental arch mode" by Huafeng Wen, filed Nov. 2, 2004, the content of which is incorporated herein by reference.

In another embodiment, the separated tooth models are assembled by geometry matching. The intact positive arch impression is first scanned to obtain a 3D digital dental arch model. Individual teeth are then scanned to obtain digital tooth models for individual teeth. The digital tooth models can be matched using rigid body transformations to match a digital dental arch model. Due to complex shape of the arch, inter-proximal areas, root of the teeth and gingival areas may be ignored in the geometry match. High precision is required for matching features such as cusps, points, crevasses, the front and back faces of the teeth. Each tooth is sequentially matched to result in rigid body transformations corresponding to the tooth positions that can reconstruct an arch.

In another embodiment, the separated tooth models are assembled and registered with the assistance of a 3D point picking devices. The coordinates of the tooth models are picked up by 3D point picking devices such as stylus or Microscribe devices before separation. Unique registration marks can be added on each tooth model in an arch before separation. The tooth models and the registration marks can be labeled by unique IDs. The tooth arch can later be assembled by identifying tooth models having the same registration marks as were picked from the Jaw. 3D point picking devices can be used to pick the same points again for each tooth model to confirm the tooth coordinates.

The base is designed in step 130 to receive the tooth models. The base and tooth models include complimentary features to allow them to be assembled together. The tooth model has a protruding structure attached to it. The features at the base and tooth models can also include a registration slot, a notch, a protrusion, a hole, an interlocking mechanism, and a jig. The protruding structure can be obtained during the casting process or be created after casting by using a CNC machine on each tooth. The positions of the receiving features in the base is determined by either the initial positions of the teeth in an arch or the desired teeth positions during a treatment process (step 140).

The digital tooth models are developed in step 150. First, the surfaces of the two physical tooth models are measured. A negative impression of a patient's teeth is obtained. A plurality of points on the surfaces of the of the negative impression is measured by a position measurement device. The coordinates of the points in three dimensional space are obtained. Details of measuring the surface positions of dental impression's surfaces are disclosed in the above referenced and commonly assigned U.S. Patent Application, titled "Producing a base for accurately receiving dental tooth models" by Huafeng Wen, and filed November 2004, and the above referenced and commonly assigned U.S. Patent Application, titled "Producing accurate base for dental arch model" by Huafeng Wen, filed November 2004.

Figure 16:
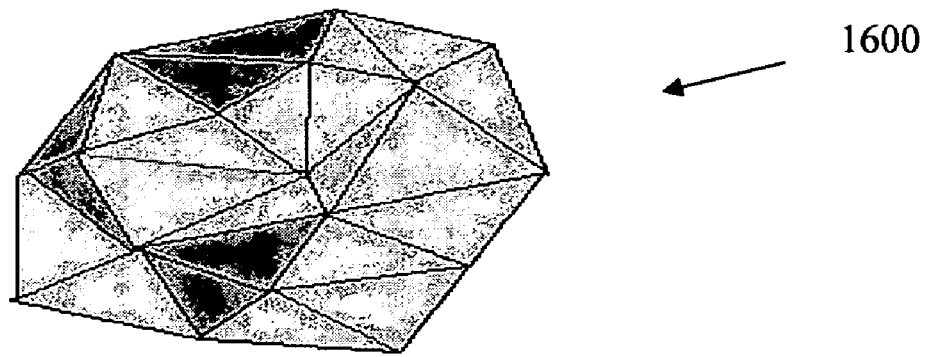
FIG. 16 illustrates a triangulated mesh that simulates the surfaces of a patient's tooth.

The plurality of points representing the surfaces of the negative impression is then used to construct a mesh to digitally represent the surfaces of the patient's teeth in three dimensions. FIG. 16 illustrates a triangulated mesh 1600 that simulates the surfaces of a patient's tooth. The mesh opening can also include other shapes with four, five or more sides or nodes. The mesh points are interpolated into one or more continuous surfaces to represent the surface of the patient's tooth, which serves as a digital model for the tooth.

Figure 17:
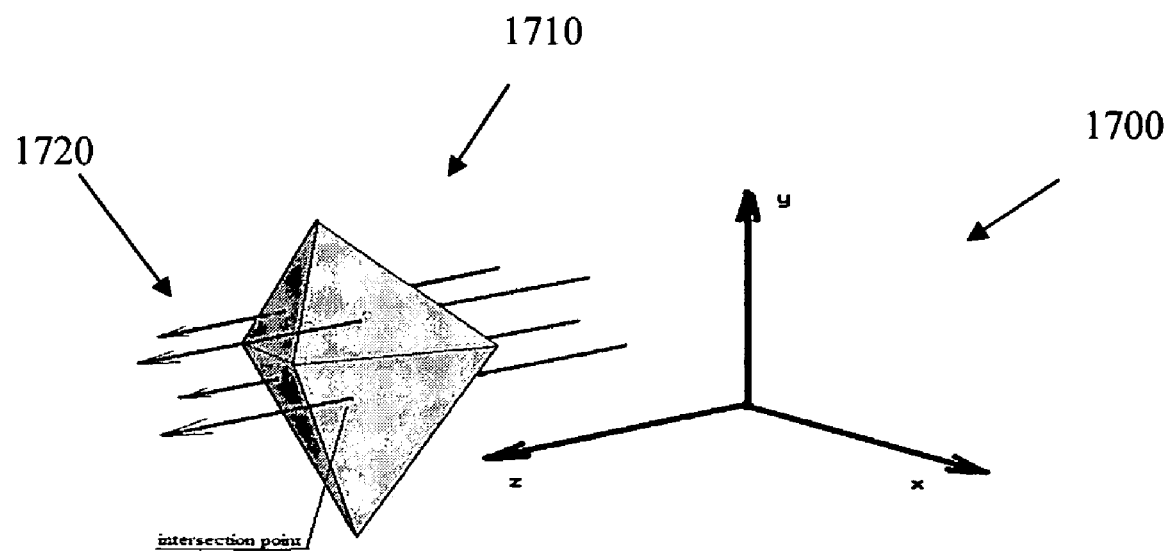
FIG. 17 illustrates the calculation of the interference depth.

The interference between two physical tooth models representing the patient's teeth can be predicted using the digital models of the two patient's teeth, in step 160. First interference depths are calculated for each digital tooth model. As shown in FIG. 17, a coordinate system 1700 comprising x, y, and z axes is established for a digital tooth model 1710. Along the z direction, as shown in FIG. 17, a plurality of lines 1720 parallel to the z-axis are specified, typically at constant intervals. The lines 1720 intersect with the surfaces of the digital tooth model 1710. The distance between the intersection points, of the segment width, of each line 1720 is called buffer width. The buffer widths are calculated along each of the x, y, and z directions.

Figure 18:
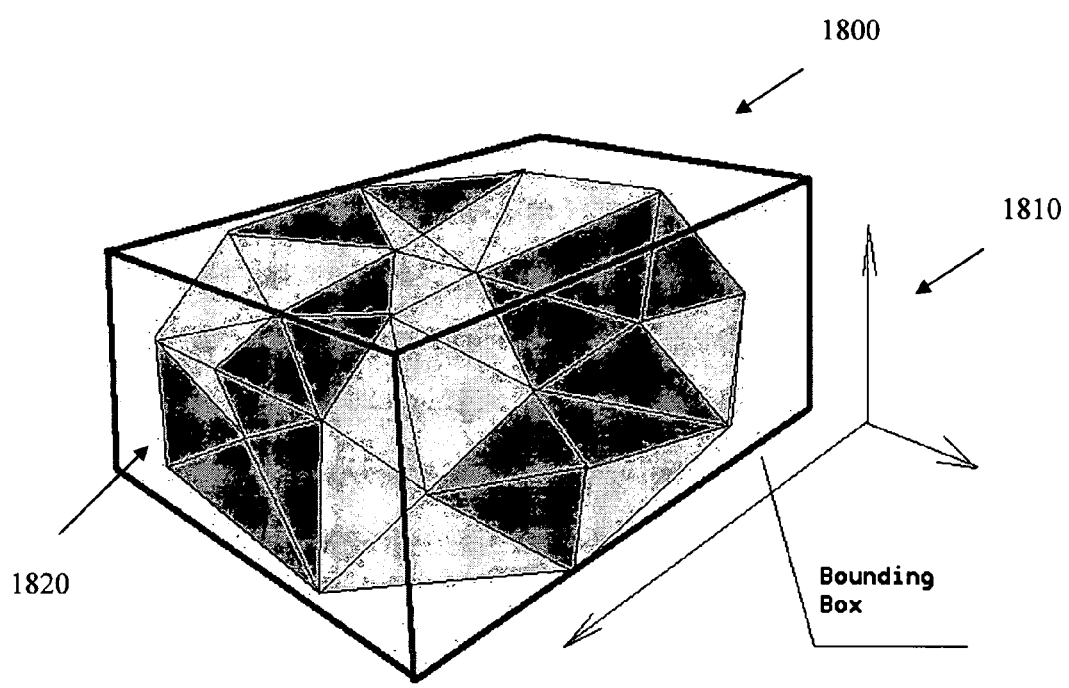
FIG. 18 illustrates the set-up of an orthogonal bounding box for calculating the interference depth.

An orthogonal bounding box 1800 can be set up as shown in FIG. 18 to assist the calculation of the buffer widths. The bounding box defines maximum range for the digital tooth model along each direction in the coordinate system 1810. The bounding box 1800 includes three pairs of rectangle faces in three directions. To calculate the buffer width along the z direction, a grid of fixed intervals is set up over the rectangular x-y face 1820 of the bounding box 1800.

Figure 19:
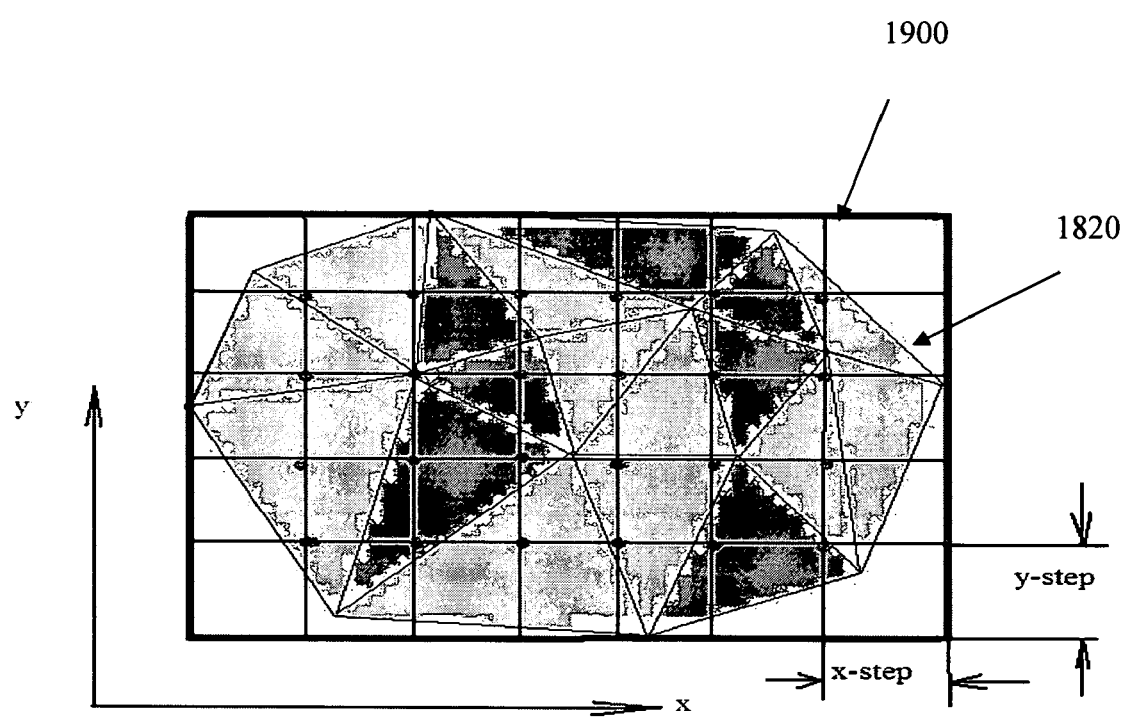
FIG. 19 shows the grid over a rectangular face of a bounding box for the digital tooth model.

The intervals of the grid 1900 along x and y direction, shown in FIG. 19, are defined in accordance with the precision requirement. The grid nodes define start and end points for the lines 1720. The grid nodes are indexed. The segment width (i.e. the buffer width) is calculated for each pair of indexed grid nodes at the two opposite rectangular faces o the bounding box 1800. The buffer widths can be rescaled and stored for example in 8 bit or 16 bit values.

Figure 20:
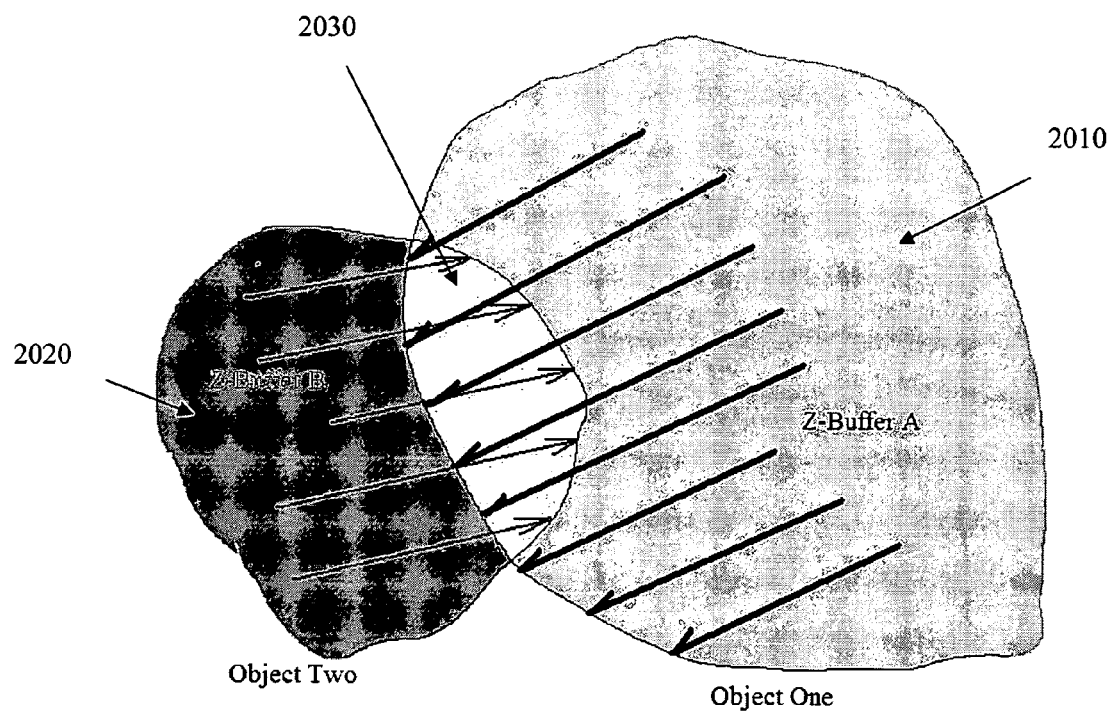
FIG. 20 illustrates the calculation of the interference depth between two tooth models.

The interference between two physical tooth models to be fabricated based on the digital tooth models can be predicted using the corresponding digital tooth models. As shown in FIG. 20, the two digital tooth models 2010 and 2020 overlap in an overlapping portion 2030. The buffer widths of each of the digital tooth models 2010 and 2020 are translated into a common coordinate system. For each of the line 1720, intersection points for each of the digital tooth models 2010 and 2020 are determined or retrieved. The interference depth or the depth of the overlapping portion 2030 can be calculated along the line in the z direction. The calculation of the interference depth is repeated for each pair of the x-y grid nodes similar to the procedure described above for each digital tooth model. The maximum interference depth can be determined among all the interference depths between the two digital tooth models.

To improve collision detection accuracy, more points will be inserted between the points of a mesh opening to interpolate the values of its neighbors. For example, a center point can be calculated by averaging the four neighbors. An edge center point can be calculated by averaging the two neighbors. Points can also be inserted by linear interpolation weighted by distances or by Spline interpolation.

Figure 21:
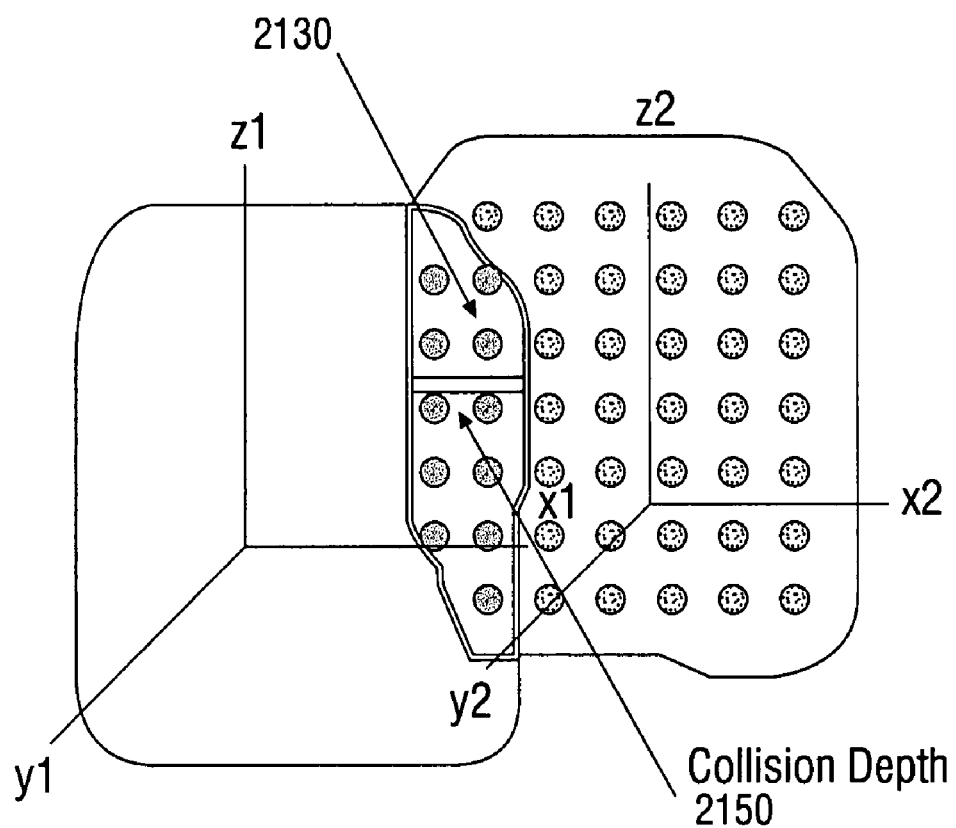
FIG. 21 illustrates two digital tooth models having aligned coordinate systems.

Sometimes the coordinate axes of two digital tooth models 2010 and 2020 of off angle than approximately parallel. The calculation of the width of the overlapping portion 2030 will not be accurate if it is based on the buffer widths of the digital tooth models 2010 and 2020. In accordance to the present invention, the coordinate systems for the digital tooth models 2010 and 2020 are translated or rotated so that their axes are aligned, as shown in the coordinate system (x1, y1, z1) and the coordinate system (x2, y2, z2) in FIG. 21. That is, the x axes, y axes and z axes are respectively parallel in the two coordinate systems. The buffer widths are then recalculated along parallel axes for the two digital tooth models 2010 and 2020 in the aligned (or common) coordinate systems. The buffer width values can therefore be additive to accurately derive the width of the overlapping portions 2150 (or collision depth, or interference depth).

Figure 22:
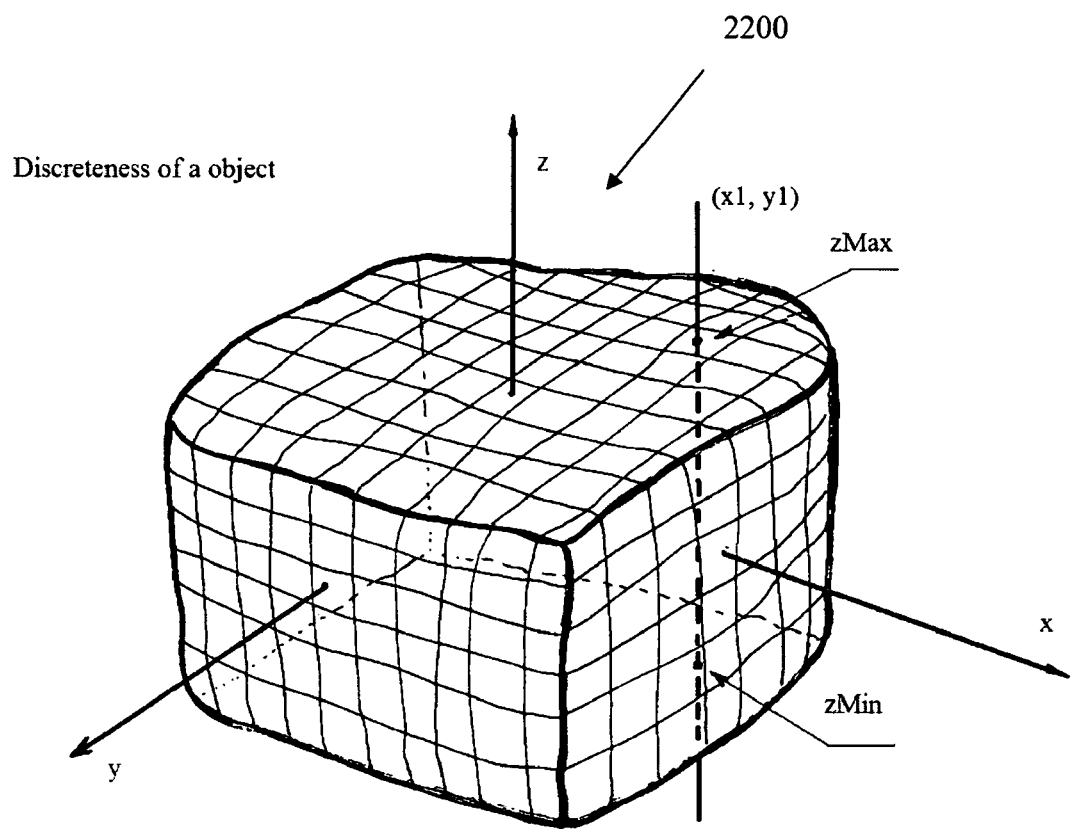
FIG. 22 illustrates the discrete digital model for an object.

The overlapping portion 2130 can be considered as a discrete three dimensional object 2200 as shown in FIG. 22. If the two coordinate systems are aligned, the width of the overlapping portion 2150 can be simply calculated by the overlapping length of the buffer widths.

Figure 23:
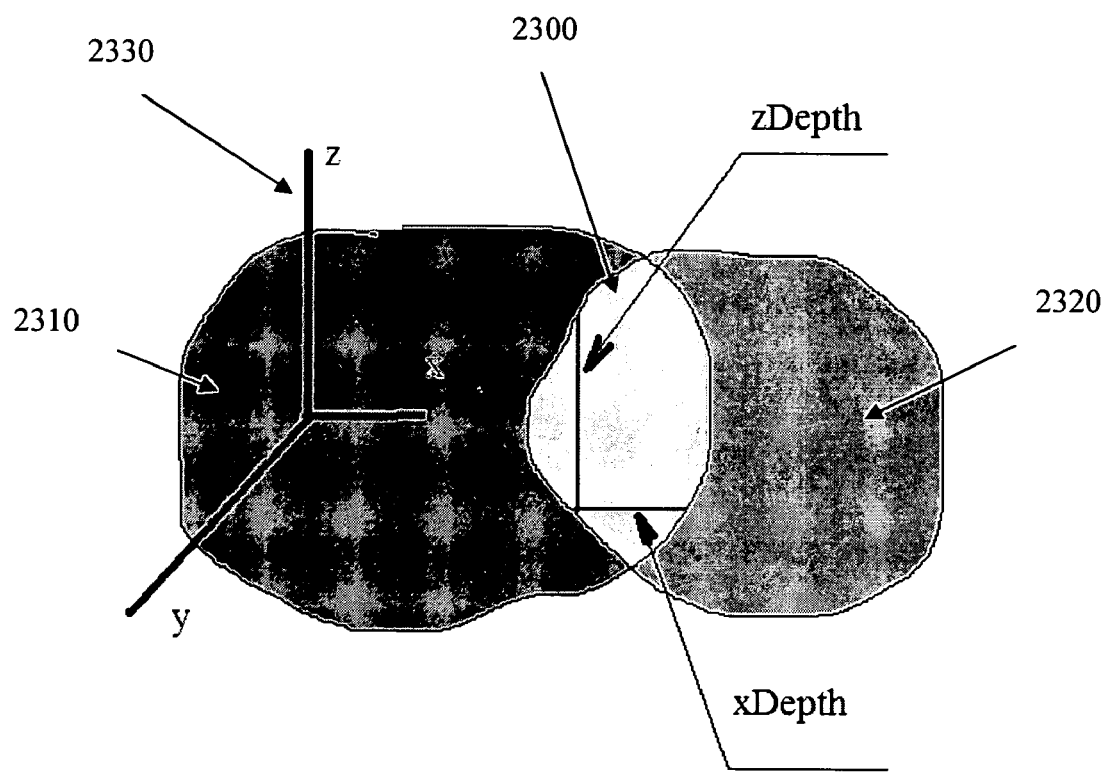
FIG. 23 illustrates the interference depth between two digital tooth models along two directions.

To more accurately describe the degree of overlapping between the two digital tooth models 2310, 2320, the widths of the overlapping portion 2300 (or the interference depths) can be separately calculated along three orthogonal directions such as along the directions of the three axes (x, y, z) of the aligned coordinate system 2330, as shown in FIG. 23. The aligned coordinate systems can also include spherical and cylindrical coordinate systems.

In accordance to the present invention, the digital tooth models that overlap can be moved apart at the design stage to prevent interference between the physical tooth models after they are fabricated and assembled. To move apart two colliding tooth models, it is desirable to select a movement direction to minimize the distance of the movement. The optimized direction is typically close to the axis of the shortest interference depth. In optimizing the movement direction, more weight is therefore given to the shorter directions of shorter interference depths. In one embodiment, as shown in FIG. 24, the vector sum 2450 of vectors 2410, 2420, 2430 respectively having magnitudes of $1/X_{depth}$, $1/Y_{depth}$, and $1/Z_{depth}$ along the x, y and x directions represent an optimized direction weighted toward directions of the shortest interference depths or shortest depth of overlapping portion.

Figure 24:
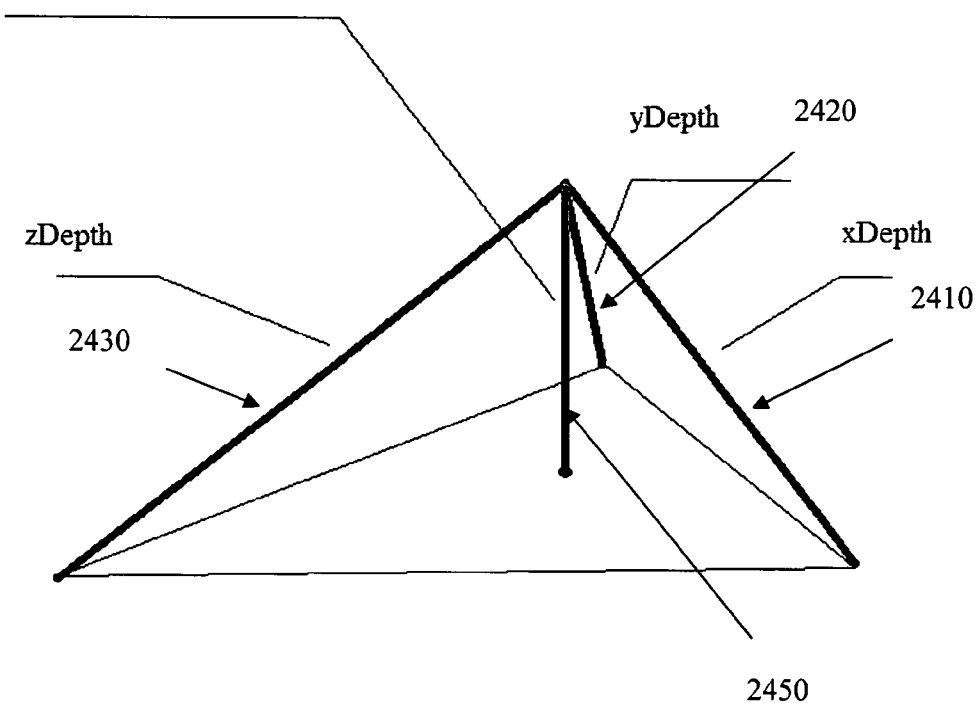
FIG. 24 illustrates the optimized direction of the interference depth between two digital tooth models in a three dimensional system.

After the optimal movement direction is determined as shown in FIG. 24, the digital tooth models 2310, 2320 are moved apart along the optimal movement direction by an amount determined by the magnitude of the vector sum 2450. In one embodiment, each of the digital tooth models 2310, 2320 moves half of the required distance of movement.

In a digital arch model involving a plurality of tooth models, adjustment movement may be required and performed on a multiple pairs of tooth models. The positional adjustment can be conducted in iterative cycles before obtaining the final arch configurations for all tooth models at a step of an orthodontic treatment. In another embodiment, a tolerance range for the gaps between the adjacent tooth models can be specified. The iterative adjustment of the tooth models will be performed until all the gaps between adjacent tooth models are within the tolerance range. The designed movement of the tooth models are recorded and will be compared to the actual movement of the teeth during the corresponding step of the treatment.

Figure 25:
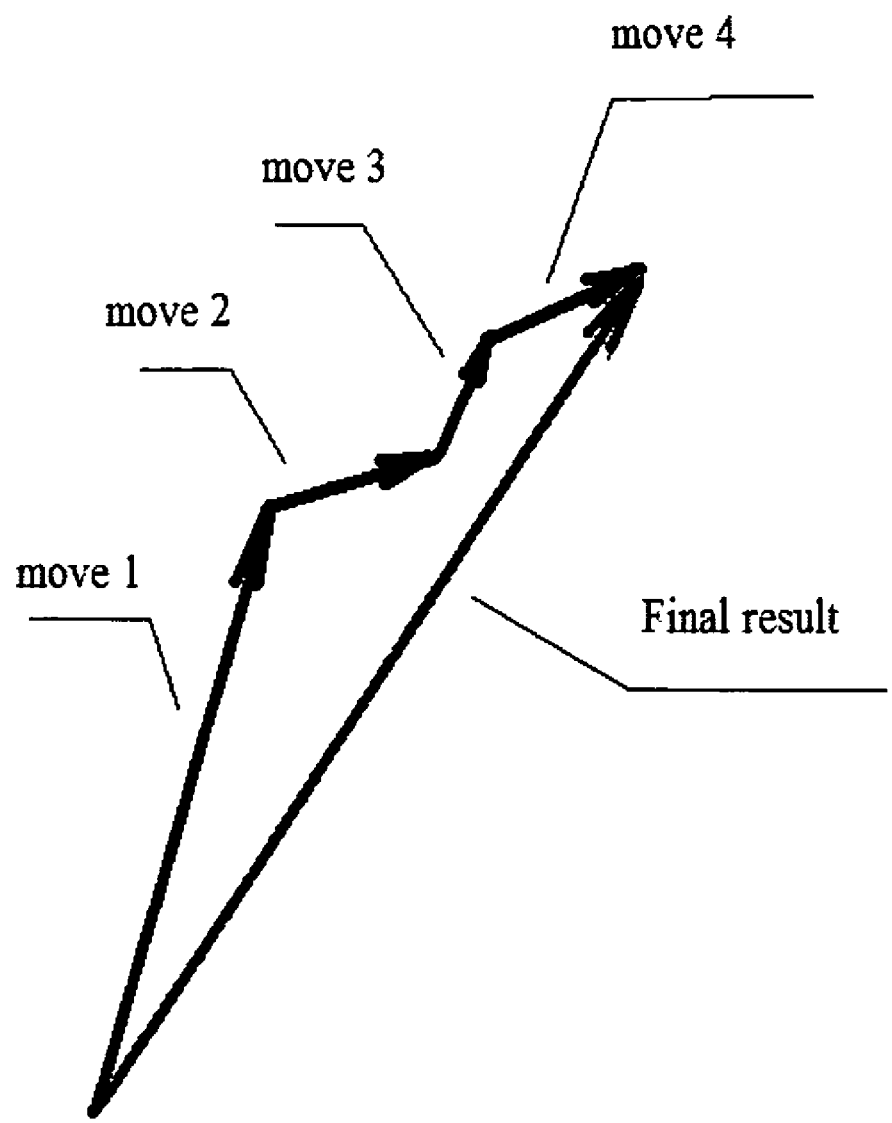
FIG. 25 illustrates the sum of the depths of interference between two digital tooth models over a multiple steps.

The total effective movement of all the movement steps of a tooth in a orthodontic treatment is the vector sum of each individual movements. As shown as FIG. 25, the total interference depth ("final result") of the orthodontic treatment is the sum of a plurality of movement vectors "move 1", "move 2", "move 3" etc. between two digital tooth models over a plurality of steps in the orthodontic treatment.

The simulation of the interference between digital tooth models serves as prediction of the interference between the physical tooth models after they are fabricated and assembled to form a physical dental base mode. The knowledge of the interference between the physical tooth models can be used to prevent such interference to occur. One method to prevent the interference is the adjust teeth positions in a dental arch model, as described above. Another method to prevent such interference is by adjusting features affixed to the physical tooth models. Both methods are valuable to an orthodontic treatment.

The tooth models can be affixed with one or more pins at their bottom portions for the tooth models to be inserted into the base. The two adjacent tooth models can interfere with each other when they are inserted into a base. The pin configurations are selected in step 170 to prevent interference between adjacent tooth models.

Figure 10:
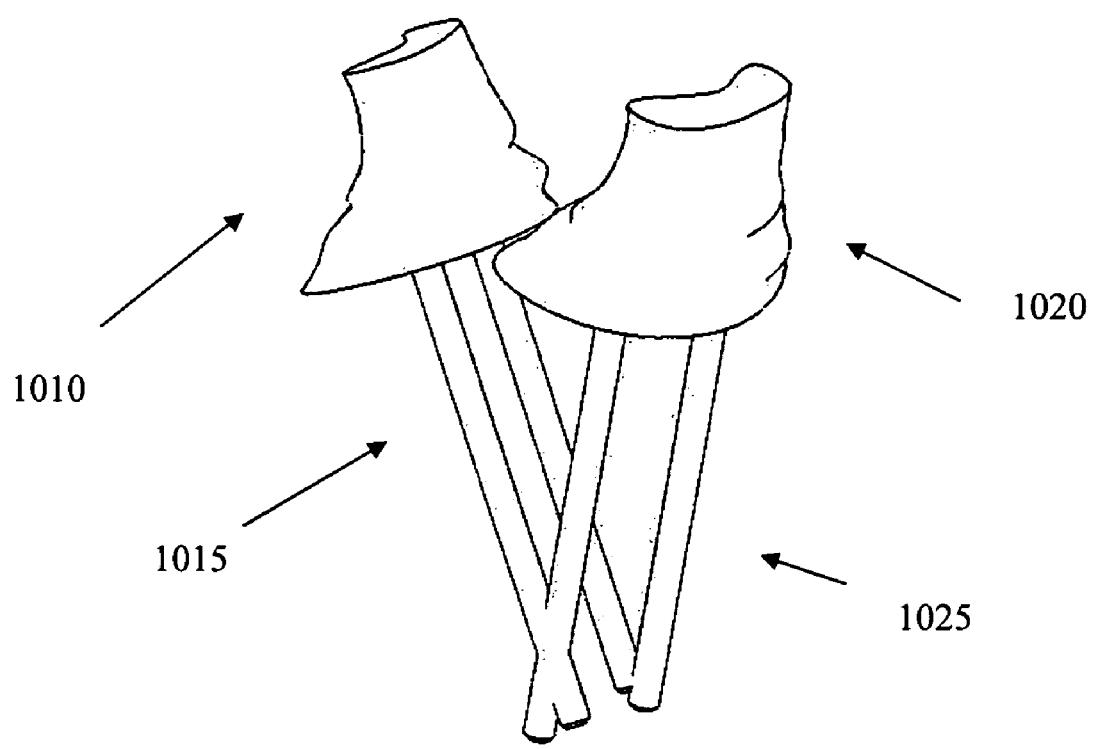
FIG. 10 illustrates an example in which the pins at the bottom portions of two adjacent tooth models interfere with each other.
Figure 11:
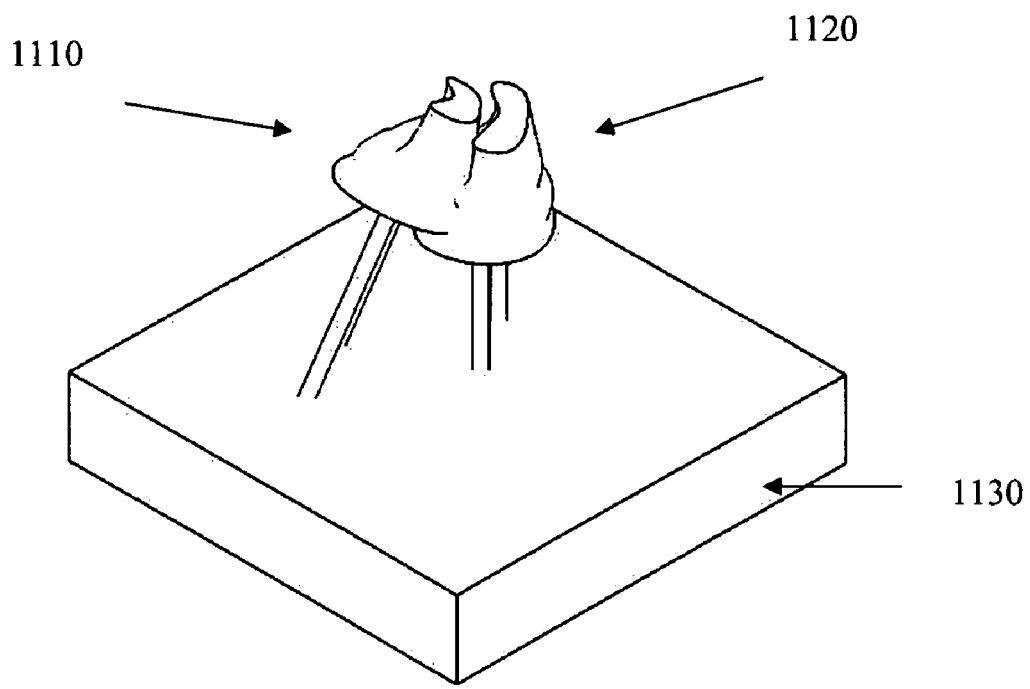
FIG. 11 illustrates an example in which two adjacent tooth models mounted on a base interfere with each other at the tooth portions of the tooth models.

Two adjacent tooth models 1010 and 1020 are shown in FIG. 10. The tooth models 1010, 1020 are respectively affixed with pins 1015 and pins 1025. The orthodontic treatment require the two adjacent tooth models 1010 and 1020 to be tilted away from each other in a tooth arch model. As a result, the pins 1015 and the pins 1025 interfere with or collide into each other. In another example, as shown in FIG. 11, two adjacent tooth models 1110 and 1120 are required to tilt toward each other by the orthodontic treatment. The tooth models 1110 and 1120 are affixed with pins having equal pin lengths. The tooth models 1110 and 1120 can collide into each other when they are inserted into a base 1130 because the insertion angles required by the long insertion pins.

Figure 12:
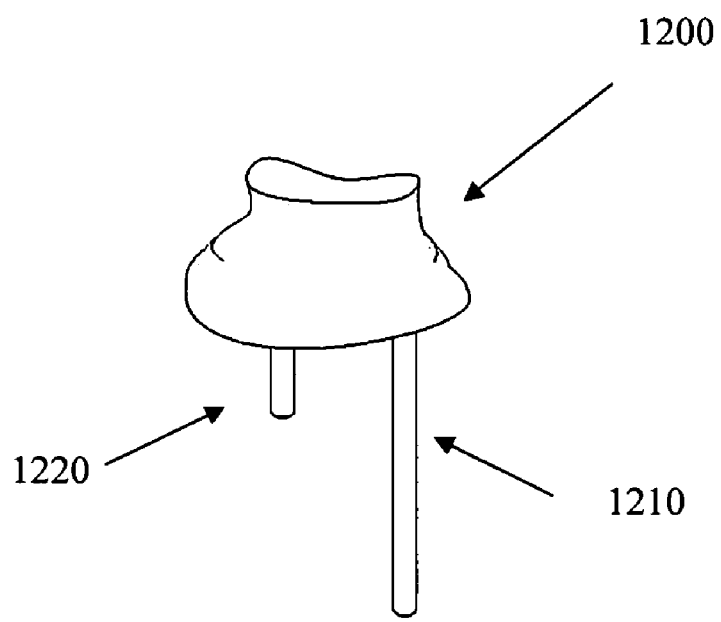
FIG. 12 illustrates a tooth model having pin configurations that prevent the tooth models from interfering with each other.

In accordance with the present invention, the interference between adjacent tooth models mounted on an arch can be resolved by properly designing and selecting configurations of the pins affixed to the bottom portion of the tooth models. FIG. 12 illustrates a tooth model 1200 having two pins 1210 and 1220 affixed to the bottom portion. To prevent interference of the tooth model 1200 with its neighboring tooth models, the pins 1210 and 1220 are designed to have different lengths.

Figure 13A:
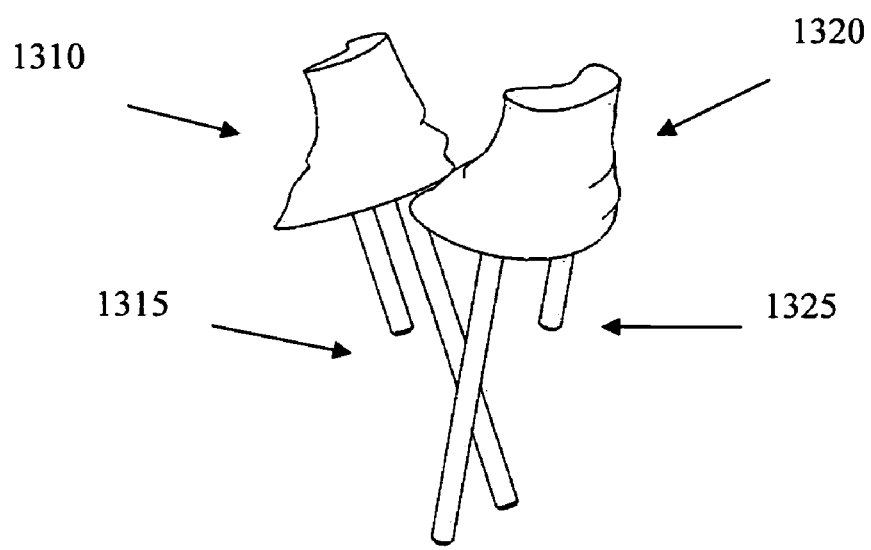
FIG. 13(*a*) is a front view of two tooth models having pin configurations of FIG. 12.
Figure 13B:
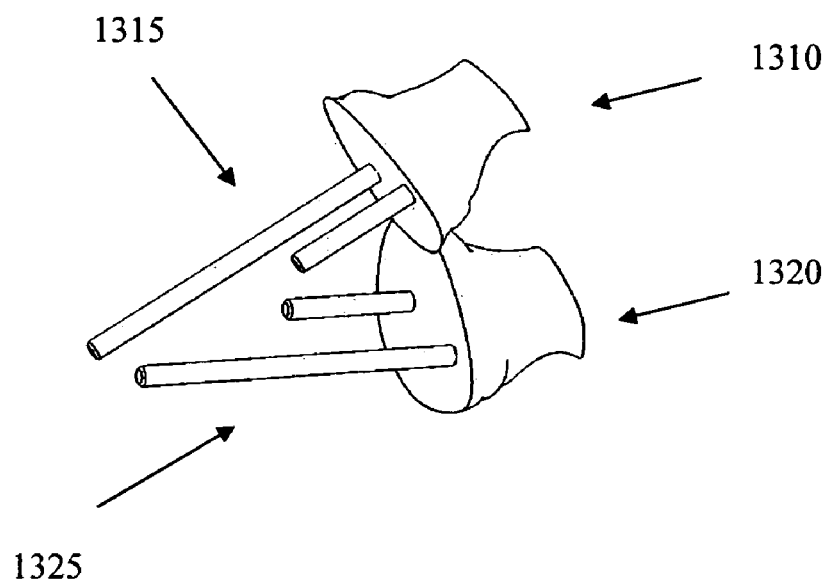

FIGS. 13(a) and 13(b) show detailed perspective views how two tooth models having the pin configurations shown in FIG. 12 can avoid interfering with each other. FIG. 13(a) shows the front perspective view of two tooth models 1310 and 1320 each of which is respectively affixed pins 1315 and 1325. The pins 1315 and pins 1325 are configured to have different lengths so that the pins do not run into each other when they are inserted into a base (not shown in FIG. 13(a) for clarity). The avoidance of interference between the tooth models 1310 and 1320 is also illustrated in a perspective bottom view in FIG. 13(b).

The pin configurations for tooth models can be selected by different methods. In one embodiment, a digital dental arch model that represents the physical tooth model is first produced or received. The digital dental arch model defines the positions and orientations of the two adjacent physical tooth models in the physical dental arch model according to the requirement of the orthodontic treatment. The positions of the physical tooth models including the pins are simulated to examine the interference between two adjacent physical tooth models mounted on the base. The pin configurations are adjusted to avoid any interference that might occur in the simulation. The pin configurations can include pins lengths, pin positions at the underside of the tooth models, and the number of pins for each tooth model.

The tooth models affixed with pins having the selected pin configurations can fabricated by Computer Numerical Control (CNC) based manufacturing in response to the digital dental arch model. At different steps of an orthodontic treatment, the tooth portions of the tooth models can remain the same while the pins affixed to the tooth portion being adjusted depending on the relative orientation of positions between adjacent tooth models. Furthermore, the base can include different socket configurations that is adapted to receive compatible pin configurations selected for different steps of the orthodontic treatment. The physical tooth models and their pin configurations can be labeled by a predetermined sequence to define the positions of the physical tooth models on the base for each step of the orthodontic treatment.

An advantage of the present invention is that the different pin configurations allow longer pins affixed to the tooth models, which results in more stable physical tooth arch model. Another advantage is that the tooth portion of the tooth models can be reused for different steps of an orthodontic treatment. Modular sockets can be prepared on the underside of the tooth models. Pins of different lengths can be plugged into the sockets to prevent interference between adjacent tooth models.

Figure 2:
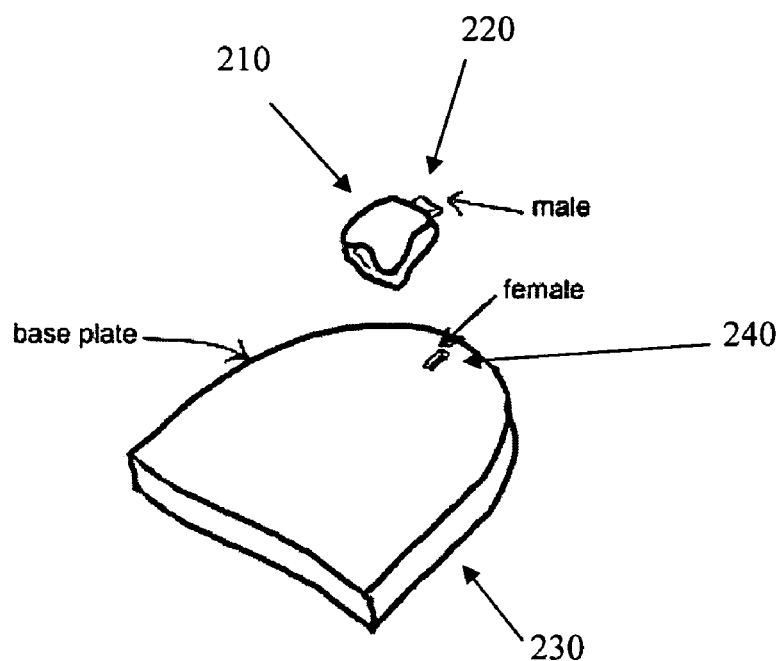
FIG. 2 illustrates a tooth model and a base respectively comprising complimentary features for assembling the tooth model with the base.

Before casting the arch from the impression, the base plate is taken through a CNC process to create the female structures for each individual tooth (step 180). Then the base is placed over the casting container in which the impression is already present and the container is filled with epoxy. The epoxy gets filled up in the female structures and the resulting mould has the male studs present with each tooth model that can be separated afterwards. FIG. 2 shows a tooth model 210 with male stud 220 after mould separation. The base 230 comprises a female feature 240 that can receive the male stud 220 when the tooth model 210 is assembled to the base 230.

Figure 3:
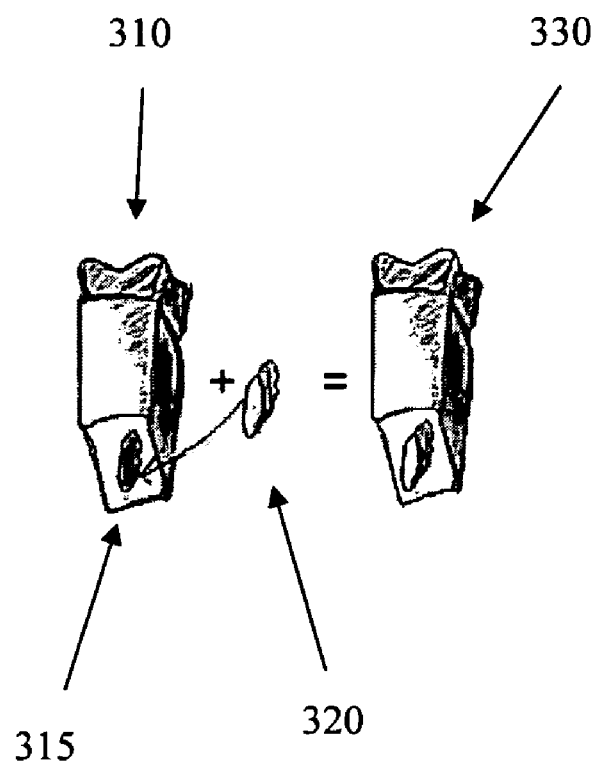
FIG. 3 illustrates fixing a stud to a tooth model comprising a female socket to produce a tooth model having a protruded stud.

Alternatively, as shown in FIG. 3, a tooth model 310 includes a female socket 315 that can be drilled by CNC based machining after casting and separation. A male stud 320 that fits the female socket 315 can be attached to the tooth model 310 by for example, screwing, glue application, etc. The resulted tooth model 330 includes male stud 310 that allows it to be attached to the base.

Figure 4:
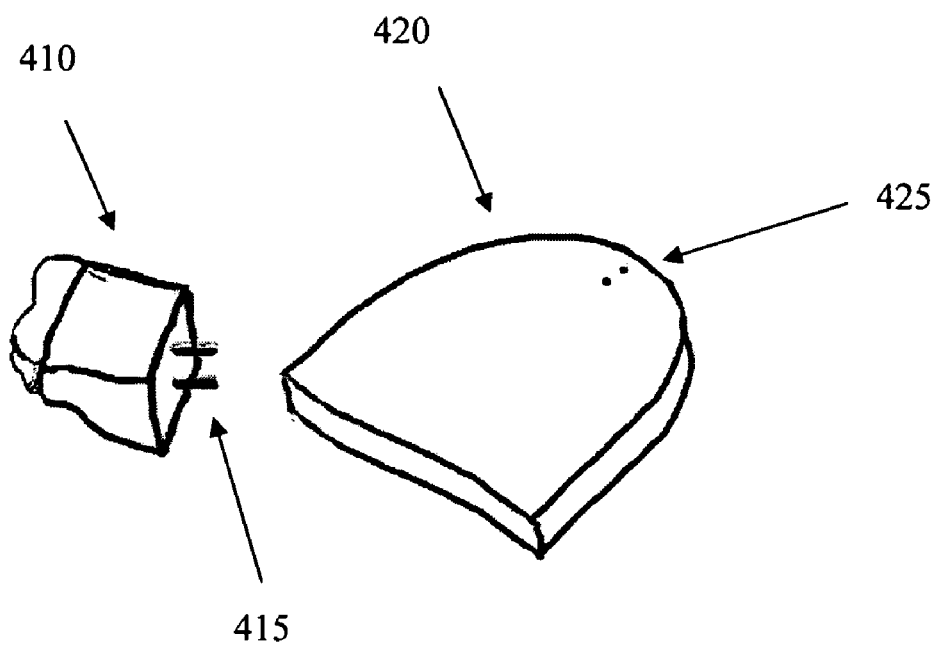
FIG. 4 illustrate a tooth model comprising two pins that allow the tooth model to be plugged into two corresponding holes in a base.
Figure 5:
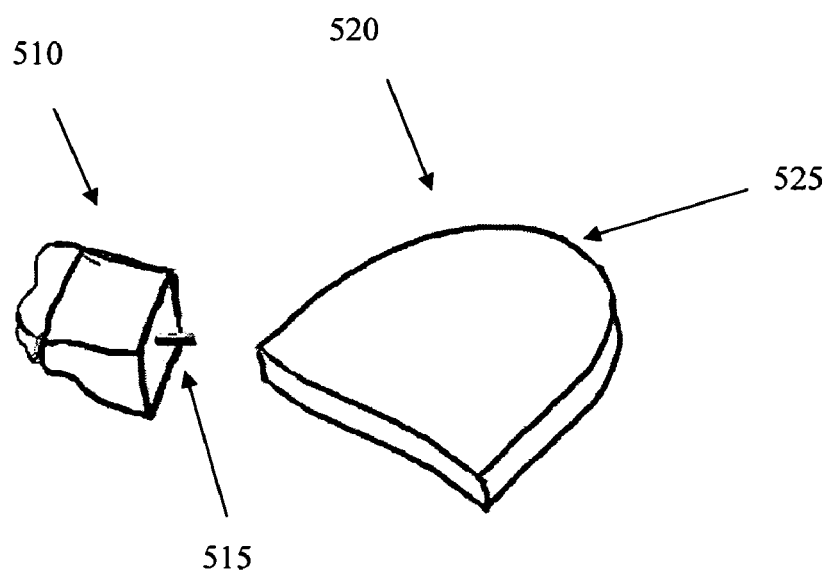
FIG. 5 illustrate a tooth model comprising a protruded pin that allows the tooth model to be plugged into a hole in a base.
Figure 6:
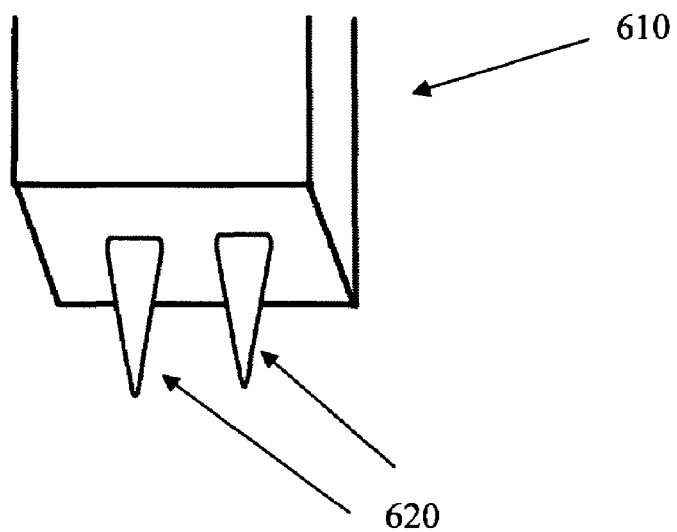
FIG. 6 illustrates cone shaped studs protruded out of the bottom of a tooth model.

Male protrusion features over the tooth model can exist in a number of arrangements. FIG. 4 shows a tooth model 410 having two pins 415 sticking out and a base 420 having registration slots 425 adapted to receive the two pins 415 to allow the tooth model 410 to be attached to the base 420. FIG. 5 shows a tooth model 510 having one pins 515 protruding out and a base 520 having a hole 525 adapted to receive the pin 515 to allow the tooth model 510 to be attached to the base 520. In general, the tooth model can include two or more pins wherein the base will have complementary number of holes at the corresponding locations for each tooth model. The tooth model 610 can also include cone shaped studs 620 as shown in FIG. 6. The studs can also take a combination of configurations described above.

Figure 7:
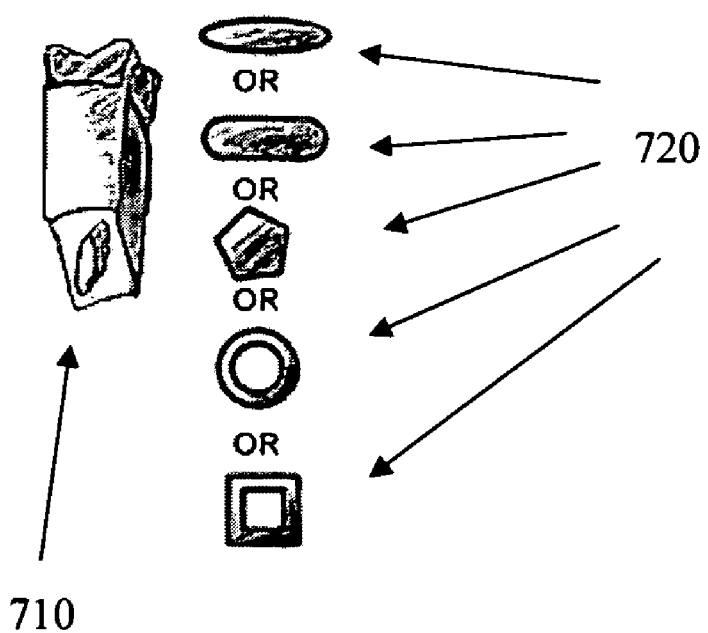
FIG. 7 illustrates exemplified shapes for the studs at the bottom of a tooth model.

As shown FIG. 7, the studs protruding our of the tooth model 710 can take different shapes 720 such as oval, rectangle, square, triangle, circle, semi-circle, each of which correspond to slots on the base having identical shapes that can be drilled using the CNC based machining. The asymmetrically shaped studs can help to define a unique orientation for the tooth model on the base.

Figure 8A:
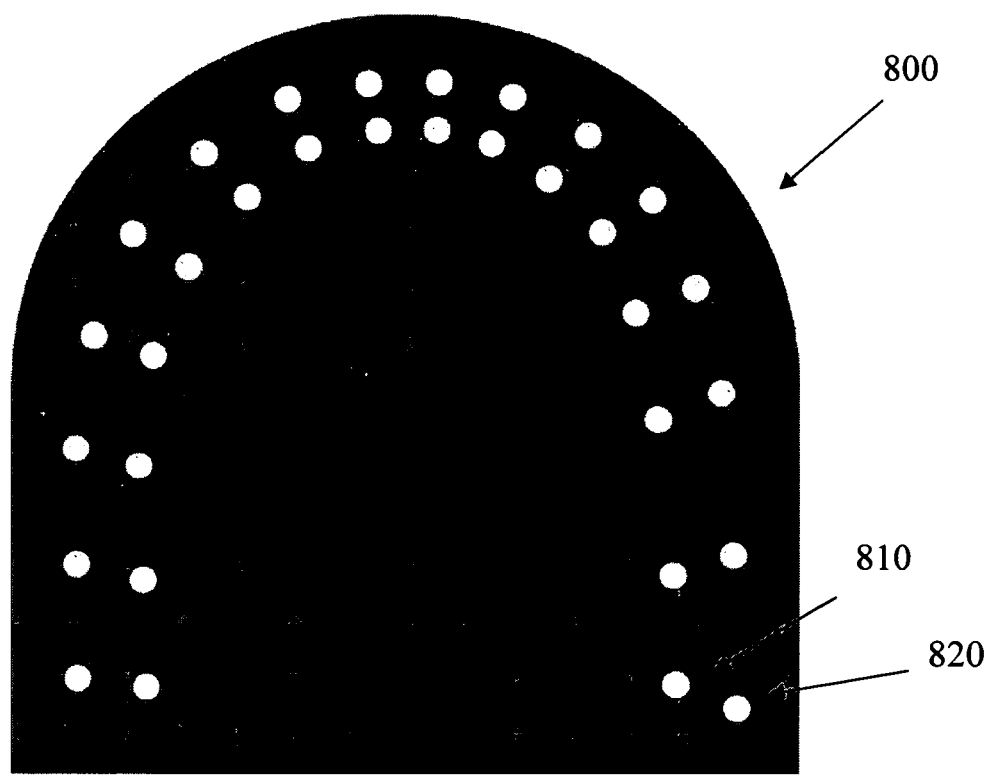
FIG. 8A illustrates an example of a base comprising a plurality of female sockets for receiving a plurality of tooth models for forming a physical dental arch model.

FIG. 8A shows a base 800 having a plurality of sockets 810 and 820 for receiving the studs of a plurality of tooth models. The positions of the sockets 810,820 are determined by either her initial teeth positions in a patient's arch or the teeth positions during the orthodontic treatment process. The base 800 can be in the form of a plate as shown in FIG. 8, comprising a plurality of pairs of sockets 810,820. Each pair of sockets 810,820 is adapted to receive two pins associated with a physical tooth model. Each pair of sockets includes a socket 810 on the inside of the tooth arch model and a socket 820 on the outside of the tooth arch model.

Figure 8B:
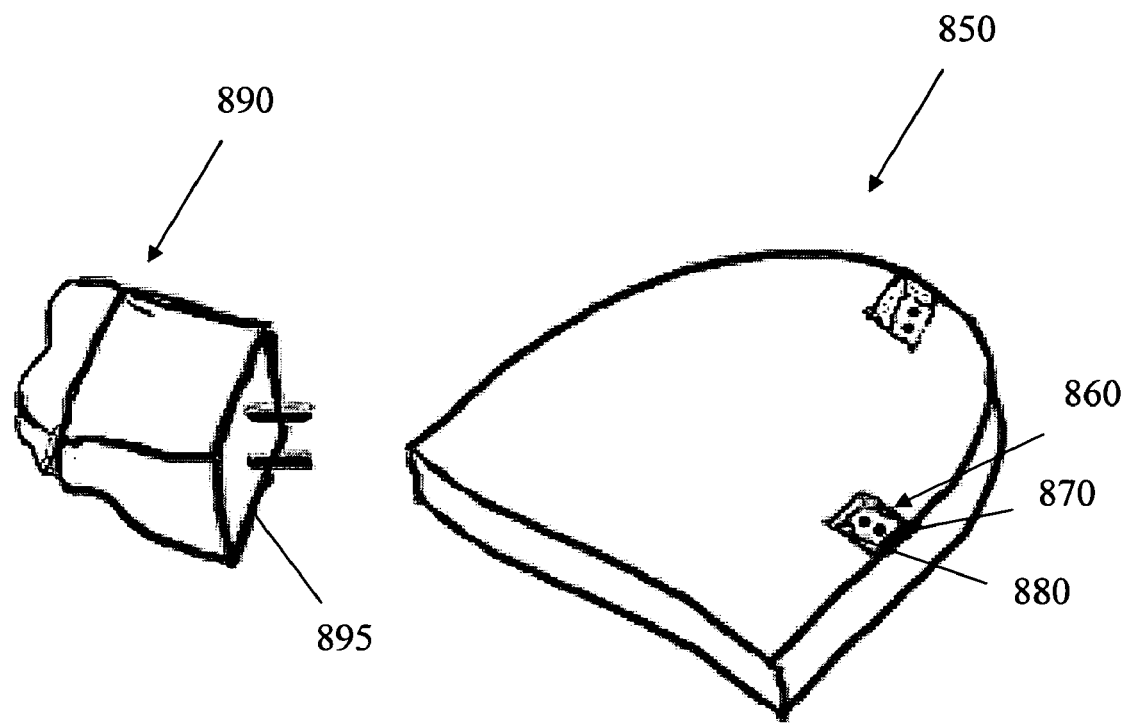
FIG. 8B illustrates another example of a base comprising a plurality of female sockets for receiving a plurality of tooth models for forming a physical dental arch model.

Another of a base 850 is shown in FIG. 8B. A plurality of pairs of female sockets 860, 870 are provided in the base 850. Each pair of the sockets 860, 870 is formed in a surface 880 and is adapted to receive a physical tooth model 890. The bottom portion of the physical tooth model 890 includes a surface 895. The surface 895 comes to contact with the surface 880 when the physical tooth model 890 is inserted into the base 850, which assures the stability of the physical tooth model 890 over the base 850.

Figure 9:
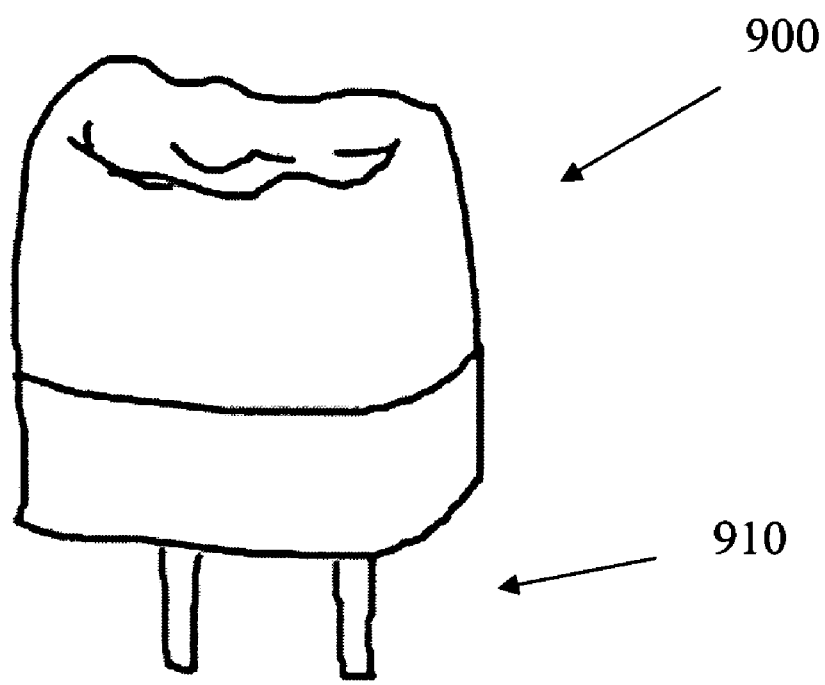
FIG. 9 illustrates a tooth model that can be assembled to the base in FIGS. 8A and 8B.

A tooth model 900 compatible with the base 800 is shown in FIG. 9. The tooth model 900 includes two pins 910 connected to its bottom portion. The two pins 910 can be plugged into a pair of sockets 810 and 820 on the base 800. Thus each pair of sockets 810 and 820 uniquely defines the positions of a tooth model. The orientation of the tooth model is also uniquely defined if the two pins are labeled as inside and outside, or the sockets and the pins are made asymmetric inside and outside. In general, each tooth model may include correspond to one or a plurality of studs that are to be plugged into the corresponding number of sockets. The male studs and the sockets may also take different shapes as described above.

Figure 14:
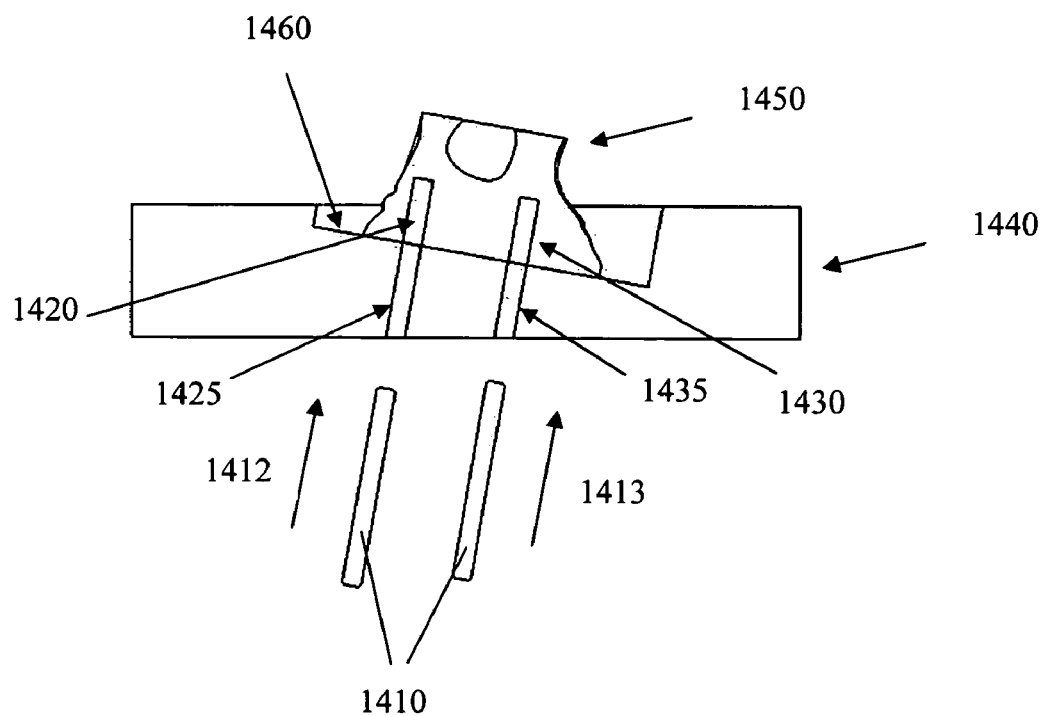
FIG. 14 illustrates a mechanism for fixing tooth models to a base using removable pins.
Figure 15:
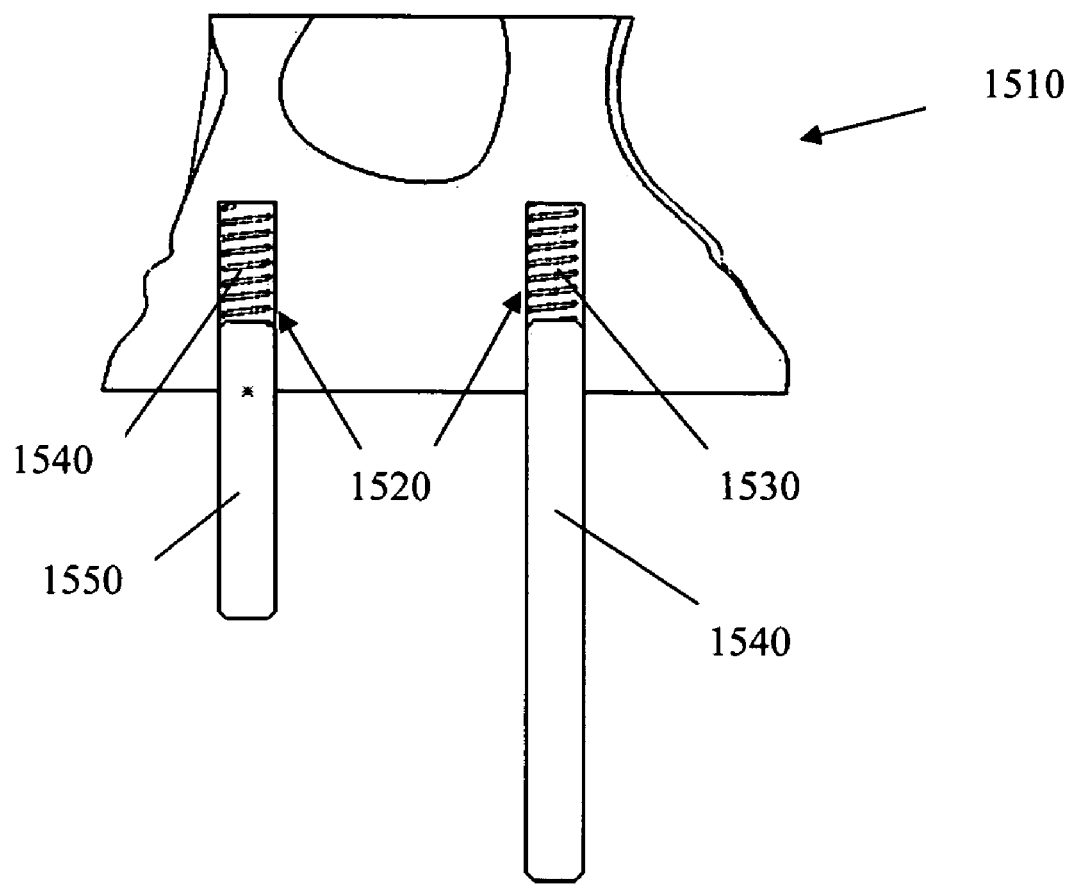
FIG. 15 illustrates a mechanism for fixing tooth models to a base using spring-loaded pins to prevent interference between tooth models.

In another embodiment, the disclosed methods and system can include teeth duplicate with removable or retractable pins, as shown in FIGS. 14 and 15. A tooth model 1450 is placed on a flat surface 1460 in a recess created in the base 1440. The base 1440 include through holes 1425 and 1435. The tooth model 1450 includes at the bottom potion drilled holes 1420 and 1430 that are in registration and alignment with the through holes 1425 and 1435. Pins 1410 can then be inserted along directions 1412, 1413 into the through holes 1425 and 1435 in the base and then holes 1420 and 1430 in the base to affix the tooth models 1450 into the base 1440.

In another embodiment, the tooth model 1510 includes holes 1520. Pins 1540 and 1550 can be inserted into the holes 1520 in spring load mechanisms 1530, 1540. The pins 1540 are retractable with compressed springs to avoid interference during insertion or after the installation of the tooth model over the base. After the tooth models are properly mounted and fixed, the pins 1540 can extend to their normal positions to maximize position and angle control. The overall pin lengths can be cut to the correct lengths to be compatible with the spring load mechanisms to prevent interference between tooth models.

The described methods are also applicable to prevent tooth model interference in precision mount of tooth models in casting chambers. In such cases, the shape and the height of the tooth models can be modified to avoid interference of teeth during insertion or at the corresponding treatment positions.

A tooth arch model is obtained after the tooth models are assembled to the base 800 (step 190). The base 800 can comprise a plurality of configurations in the female sockets 810. Each of the configurations is adapted to receive the same physical tooth models to form a different arrangement of at least a portion of a tooth arch model.

The base 800 can be fabricated by a system that includes a computer device adapted to store digital tooth models representing the physical tooth models. As described above, the digital tooth model can be obtained by various scanning techniques. A computer processor can then generate a digital base model compatible with the digital tooth models. An apparatus fabricates the base using CNC based manufacturing in accordance with the digital base model. The base fabricated is adapted to receive the physical tooth models.

The physical tooth models can be labeled by a predetermined sequence that define the positions of the physical tooth models on the base 800. The labels can include a barcode, a printed symbol, hand-written symbol, a Radio Frequency Identification (RFID). The female sockets 810 can also be labeled by the parallel sequence for the physical tooth models.

In one embodiment, tooth models can be separated and repaired after the base. The tooth models can be removed, repaired or replaced, and re-assembled without the replacement of the whole arch model.

Common materials for the tooth models include polymers, urethane, epoxy, plastics, plaster, stone, clay, acrylic, metals, wood, paper, ceramics, and porcelain. The base can comprise a material such as polymers, urethane, epoxy, plastics, plaster, stone, clay, acrylic, metals, wood, paper, ceramics, porcelain, glass, and concrete.

The arch model can be used in different dental applications such as dental crown, dental bridge, aligner fabrication, biometrics, and teeth whitening. For aligner fabrication, for example, each stage of the teeth treatment may correspond a unique physical dental arch model. Aligners can be fabricated using different physical dental arch models one at a time as the teeth movement progresses during the treatment. At each stage of the treatment, the desirable teeth positions for the next stage are calculated. A physical dental arch model having modified teeth positions is fabricated using the process described above. A new aligner is made using the new physical dental arch model.

In accordance with the present invention, each base is specific to an arch configuration. There is no need for complex and costly mechanisms such as micro-actuators for adjusting multiple degrees of freedom for each tooth model. The described methods and system is simple to make and easy to use.

The described methods and system are also economic. Different stages of the arch model can share the same tooth models. The positions for the tooth models at each stage of the orthodontic treatment can be modeled using orthodontic treatment software. Each stage of the arch model may use a separate base. Or alternatively, one base can be used in a plurality of stages of the arch models. The base may include a plurality of sets of receptive positions for the tooth models. Each set corresponds to one treatment stage. The tooth models can be reused through the treatment process. Much of the cost of making multiple tooth arch models in orthodontic treatment are therefore eliminated.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A method for preventing interference between two physical tooth models in a physical dental arch model, comprising:

digitally representing the surfaces of each of the two physical tooth models by a mesh of points in three dimensions;

interpolating the meshes of points to produce interpolated surfaces to represent the boundaries of the two physical tooth models, wherein the interpolated surfaces representing the boundaries of the two physical tooth models intersect at least at one point to form an overlapping portion;

specifying a straight line running through the overlapping portion and intersecting the two interpolated surfaces representing the boundaries of the two physical tooth models; and calculating the length of the straight line in the overlapping portion to quantify the interference between the two physical tooth models.

2. The method of claim 1, further comprising acquiring the coordinates of a plurality of points on the surfaces of each of the two physical tooth models; and digitally representing the surfaces of each of the two physical tooth models by a mesh of points in three dimensions using the acquired coordinates.

3. The method of claim 2, further comprising measuring the positions of points on the surfaces of an impression representing a patient's teeth.

4. The method of claim 1, further comprising
developing aligned coordinate systems or a common coordinate system for the two interpolated surfaces representing the boundaries of the two physical tooth models wherein the straight line can be quantitative defined.

5. The method of claim 1, further comprising
calculating the lengths of three orthogonally oriented straight lines in the overlapping portion;
defining three vectors along the three orthogonally oriented straight lines, each of the vectors having a magnitude of the inverse of the length in the overlapping portion; and
calculating a vector sum of the three vectors to determine the direction and the distance required for the interpolated surfaces representing the two physical tooth models to move apart to avoid interference between the two physical tooth models.

6. The method of claim 5, further comprising
moving apart the interpolated surfaces representing the boundaries of the two physical tooth models in accordance to the vector sum to avoid interference between the two physical tooth models.

7. The method of claim 1, further comprising adjusting the positions or the orientations of at least one of the two physical tooth models to prevent the interference between the physical tooth models.

8. The method of claim 1, wherein at least one of the meshes comprises at least one mesh opening having three, four or five nodes.

9. The method of claim 1, further comprising selecting the configurations of a first feature to be affixed to the undersides of the two physical tooth models to prevent interference between the two physical tooth models when they are mounted to a base with the assistance of the first feature.

10. The method of claim 9, wherein the second feature comprises one or more of a pin, a registration slot, a socket, a notch, a protrusion, a hole, an interlocking mechanism, a jig, and a pluggable or an attachable feature.

11. The method of claim 9, further comprising fabricating the physical tooth models having the first features having the selected configurations.

12. The method of claim 1, further comprising selecting the positions and orientations of second features on a base to prevent interference between the two physical tooth models when they are mounted to a base with the assistance of the second features.

13. The method of claim 12, wherein the second feature comprises one or more of a pin, a registration slot, a socket, a notch, a protrusion, a hole, an interlocking mechanism, a jig, and a pluggable or an attachable feature.

14. The method of claim 12, further comprising
fabricating the base having the second features having the selected positions and orientations.

15. A method for preventing interference between two physical tooth models in a physical dental arch model, comprising:
digitally representing the surfaces of each of the two physical tooth models by a mesh of points in three dimensions;
interpolating the meshes of points to produce interpolated surfaces to represent the boundaries of the two physical tooth models, wherein the interpolated surfaces representing the two physical tooth models intersect at least at one point to form an overlapping portion;
developing aligned coordinate systems or a common coordinate system for the two interpolated surfaces representing the two physical tooth models;
specifying a straight line running through the overlapping portion and intersecting the two interpolated surfaces representing the boundaries of the two physical tooth models; and
calculating the length of the straight line in the overlapping portion to quantify the interference between the two physical tooth models.

16. The method of claim 15, further comprising
calculating the lengths of three orthogonally oriented straight lines in the overlapping portion;
defining three vectors along the three orthogonally oriented straight lines, each of the vectors having a magnitude of the inverse of the length in the overlapping portion; and
calculating a vector sum of the three vectors to determine the direction and the distance required for the interpolated surfaces representing the boundaries of the two physical tooth models to move apart to avoid interference between the two physical tooth models.

17. The method of claim 16, further comprising
moving apart the interpolated surfaces representing the boundaries of the two physical tooth models in accordance to the vector sum to avoid interference between the two physical tooth models.

18. The method of claim 15, further comprising selecting the configurations of a first feature to be affixed to the undersides of the two physical tooth models to prevent interference between the two physical tooth models when they are mounted to a base with the assistance of the first feature.

19. The method of claim 18, wherein the second feature comprises one or more of a pin, a registration slot, a socket, a notch, a protrusion, a hole, an interlocking mechanism, a jig, and a pluggable or an attachable feature.

20. A method for preventing interference between two physical tooth models in a physical dental arch model, comprising:
digitally representing the surfaces of each of the two physical tooth models by a mesh of points in three dimensions;
interpolating the meshes of points to produce interpolated surfaces to represent the boundaries of the two physical tooth models, wherein the interpolated surfaces representing the boundaries of two physical tooth models intersect at least at one point to form an overlapping portion;
specifying three orthogonally oriented straight lines each running through the overlapping portion and intersecting the two interpolated surfaces representing the boundaries of the two physical tooth models;
calculating the lengths of three orthogonally oriented straight lines in the overlapping portion;
defining three vectors along the three orthogonally oriented straight lines, each of the vectors having a magnitude of the inverse of the corresponding length of the overlapping portion;
calculating a vector sum of the three vectors to determine the direction and the distance required for the interpolated surfaces representing the boundaries of the two physical tooth models to move apart to avoid interference between the two physical tooth models; and
moving apart the interpolated surfaces representing the boundaries of the two physical tooth models in accordance to the vector sum to avoid interference between the two physical tooth models.

* * * * *